United States Patent [19]

Dedieu et al.

[11] Patent Number: 5,329,045

[45] Date of Patent: Jul. 12, 1994

[54] PROCESS FOR DEODORISING A MERCAPTO ACID BY EXTRACTING MALODOROUS COMPOUNDS THEREFROM WITH CARBON DIOXIDE

[75] Inventors: Michel Dedieu, Maisons Laffitte; Herve Burgaud, Dammartin en Goele; Eric LaPoirie, Villemomble; Véronique Gurfein, Le Plessis Robinson; Gérard Malle, Villiers-Sur-Morin, all of France

[73] Assignee: L'Oreal, Paris, France

[21] Appl. No.: 45,140

[22] Filed: Apr. 12, 1993

[30] Foreign Application Priority Data

Oct. 15, 1992 [FR] France ............... 92 12345

[51] Int. Cl.$^5$ ............................................. C07C 51/42
[52] U.S. Cl. ................................. 562/593; 562/606; 562/512
[58] Field of Search ................... 562/593, 606, 512

[56] References Cited

U.S. PATENT DOCUMENTS

| | | | |
|---|---|---|---|
| 2,398,485 | 4/1946 | Wilson | 562/593 |
| 2,402,825 | 6/1946 | Lovell et al. | 562/593 |
| 2,425,226 | 8/1947 | Bearse | 562/593 |
| 2,824,135 | 2/1958 | Corcoran | 562/593 |
| 2,837,565 | 6/1958 | Feldman et al. | 562/593 |
| 3,290,369 | 12/1966 | Bonfield | 562/593 |
| 3,320,230 | 5/1987 | Bennett | 562/593 |
| 4,014,903 | 3/1977 | Moore | 562/593 |
| 4,902,828 | 2/1990 | Wickenhaeuser | 562/577 |
| 4,902,829 | 2/1990 | Kulprtahipanja | 562/580 |
| 5,034,509 | 7/1991 | Revaskz | 562/593 |

FOREIGN PATENT DOCUMENTS 464215 4/1950 Canada .
1276642 6/1972 United Kingdom .

OTHER PUBLICATIONS

Patent Abstracts of Japan, vol. 8, No. 114 (C-225) May 26, 1984, JP-A-57 027 866 (Raion) Feb. 14, 1984.

*Primary Examiner*—Paul J. Killos
*Attorney, Agent, or Firm*—Cushman, Darby & Cushman

[57] ABSTRACT

A process for deodorizing a mercapto acid or a polar solvent solution thereof includes extracting malodorous compounds present therein by extraction with carbon dioxide in gaseous, liquid or solid form. The mercapto acid has the formula HS-A-COOH wherein A represents

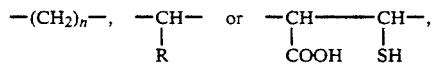

wherein n is an integer ranging from 1–4 and R is linear or branched $C_1$–$C_3$ alkyl.

13 Claims, 1 Drawing Sheet

PROCESS FOR DEODORISING A MERCAPTO ACID BY EXTRACTING MALODOROUS COMPOUNDS THEREFROM WITH CARBON DIOXIDE

The present invention relates to a process for deodorizing a mercapto acid by extraction of the malodorous compounds, and to the deodorized product thereby obtained.

BACKGROUND OF THE INVENTION

Mercapto acids are well-known derivatives which have a thiol (—SH) function and an acid (—COOH) function. They have many applications. Thioglycolic (or mercaptoacetic) acid, for example, may be used in its acid form as an intermediate in the synthesis of many pesticides and pharmaceutical products, or in its acid or salified ( especially ammonium, amine, sodium, potassium or calcium salt) form for the pickling of metal surfaces, the treatment of sulphide ores and the treatment of leathers and hides; in the cosmetics industry, it also constitutes the most widely used reducing agent for the permanent-reshaping of hair (curling or straightening) and the main active substance in depilatory milks and creams. Similarly, thiolactic acid (2-mercaptopropionic acid) is used as a reducing agent for the permanent-reshaping of hair or as a constituent of depilatory milks and creams.

Pure mercapto acids have a slight pungent odor which is not really unpleasant. However, they always contain sulphide compounds such as hydrogen sulphide and low molecular weight mercaptans, especially methanethiol or ethanethiol, which have an especially unpleasant nauseating odor. Very small amounts of these sulphide compounds are sufficient for their presence to be detected using one's sense of smell, the nose being, in this case, the best instrument of detection.

The presence of these malodorous compounds is associated with various processes of decomposition of the mercapto acids, which processes are still very poorly understood but are doubtless due to both ionic and free-radical mechanisms that can take place when air is absent. This decomposition and the resulting formation of malodorous compounds can, moreover, be monitored over time by various analytical techniques, especially by the so-called headspace method in gas chromatography.

In the various applications, and more especially in their cosmetic applications, the odor emitted by mercapto acids constitutes a genuine nuisance to the users. An effort has hence been made to mask the odor of mercapto acids by perfumes, but this odor is, in general, too powerful to be amenable to satisfactory masking. The proposal has also been made, in Japanese Patent Application No. 82-136,280 published under No. 84/027,866, to deodorise thioglycolic acid, pure or mixed with water, by extraction with a $C_4$–$C_8$ non-aromatic hydrocarbon. However, it was found that, while this extraction process enables the malodorous compounds to be extracted and a deodorized acid to be obtained, the deodorization effect obtained is not lasting with the passage of time, since the malodorous compounds quickly re-form and cancel out the benefit obtained by the treatment; in some cases, the odor even returns at a higher level than the initial level.

SUMMARY OF THE INVENTION

The invention relates to a process for extracting the malodorous compounds from mercapto acids, which enables a deodorized mercapto acid to be obtained, the deodorization effect being lasting.

The subject of the present invention is hence a process for deodorization a mercapto acid by extraction of the greater part of the malodorous decomposition products contained in the mercapto acid subjected to the treatment, characterized in that the mercapto acid treated is of the formula:

$$HS-A-COPOH \qquad (I)$$

in which formula A represents
the divalent radical

where n is an integer between 1 and 4,
the divalent radical

where R represents a linear or branched $C_1$–$C_3$ alkyl radical, or
the divalent radical

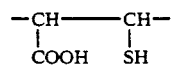

and in that the extraction is performed using carbon dioxide in the gaseous, liquid or solid state.

The mercapto acid treated is preferably thioglycolic acid or thiolactic acid; 4-mercaptobutyric acid, 3-mercaptopropionic acid and dimercaptosuccinic acid may, however, also be mentioned.

DETAILED DESCRIPTION

Figure 1:
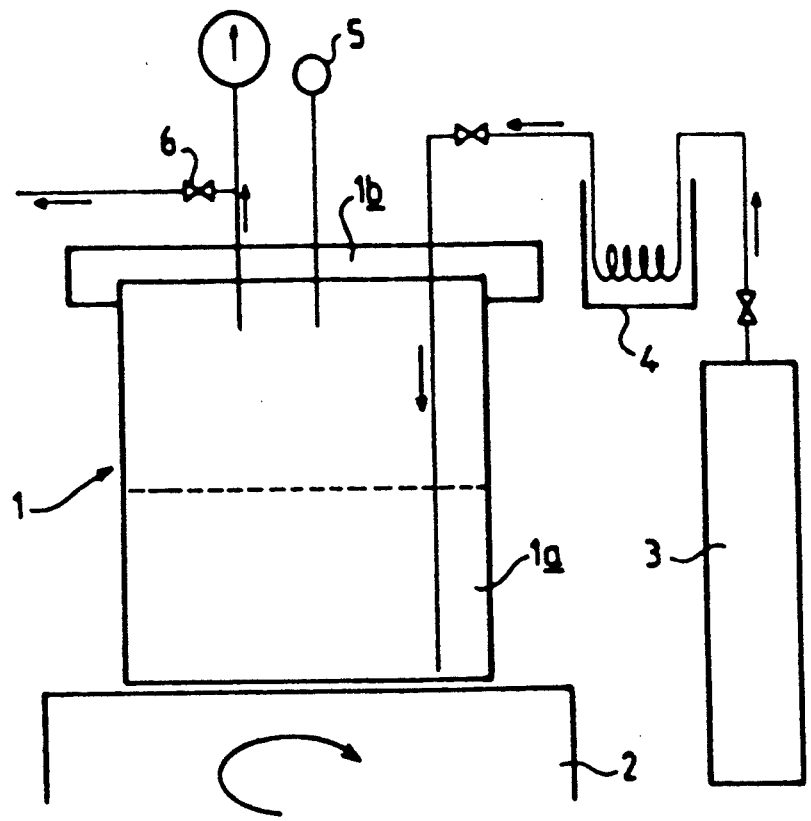
FIG. 1 is a flow diagram of a discontinuous extraction process.

According to this extraction process, the carbon dioxide becomes loaded with malodorous compounds, and the deodorized mercapto acid is obtained as a liquid extraction residue. The mercapto acid obtained was found to be completely deodorized: in effect, it now has only its distinctive slightly pungent odor; furthermore, an assay of hydrogen sulphide and of methanethiol by so-called headspace gas chromatography shows that these compounds have been completely removed. Moreover, it was quite unexpectedly found that, after two months of storage of the deodorized mercapto acid at room temperature and protected from the air, the human sense of smell does not enable the presence of malodorous compounds to be detected. Consequently, the latter are not re-formed, or are re-formed only in very small proportions. It should be noted that the deodorized mercapto acid is not necessarily pure: it could contain odorless impurities.

The extraction is performed by contact of the mercapto acid, where appropriate in solution, with gaseous, liquid or solid carbon dioxide. The solid carbon dioxide is, in particular, in the form of "dry ice". It should be noted that a portion of this carbon dioxide can possibly be in the supercritical state at a given instant during the extraction process.

The extraction temperatures and pressures used are chosen so as to maintain all or part of the carbon dioxide outside the supercritical region bounded by the critical temperature point which is 31° C. and the critical pressure point which is $73.8 \times 10^5$ pascals.

Since mercapto acids are, in general, liquid products at room temperature, the extraction can be performed by direct contact of the acid with $CO_2$. However, it is possible to use a solution of mercapto acid in a solvent, especially a polar solvent.

The polar solvent is preferably chosen from the group composed of water, linear or branched $C_1$–$C_5$ monohydric alcohols, $C_2$–$C_6$ diols, $C_3$–$C_6$ polyols and mixtures thereof. Water is the preferred solvent since, in most applications, its subsequent removal is not necessary.

The monohydric alcohol may be chosen from the group composed of methanol, ethanol, 1-propanol, 2-propanol, 1-butanol, 2-butanol, 2-methylpropanol and 1-pentanol.

The diol is advantageously chosen from the group composed of ethylene glycol, 1,2-propanediol, 1,3-propanediol, 1,3-butanediol, 2,3-butanediol and 1,6-hexanediol.

The polyol can advantageously be glycerol.

In the case where the mercapto acid is in solution form, the solvent may be used in amounts of between 1 and 99% by weight relative to the mercapto acid. It is preferable to use aqueous, alcoholic or aqueous-alcoholic solutions having a mercapto acid concentration of between 0.1 mol/liter and 14 mol/liter, and preferably between 1 mol/liter and 10 mol/liter.

The extraction may be performed in the presence of an inert gaseous compound such as helium, nitrogen or argon. The extraction yield with respect to the amount of $CO_2$ employed is thereby improved.

When the carbon dioxide is in gas or liquid form, the extraction may be performed either in continuous, in semi-continuous and in discontinuous fashion. When the carbon dioxide is in solid form, the procedure is preferably carried out in discontinuous fashion.

When the procedure is carried out in discontinuous fashion, the mercapto acid, where appropriate a solvent, carbon dioxide in gaseous, liquid or solid form and, where appropriate, an inert gas are introduced into a reactor; it is arranged for the pressure and temperature conditions desired for the extraction to be obtained. The constituents are left in contact for 5 to 30 minutes and the carbon dioxide is then drawn off. Two or more extraction cycles are performed where appropriate, reintroducing carbon dioxide, reestablishing the temperature and pressure conditions desired for the extraction, leaving the constituents in contact and evacuating the $CO_2$. At the end of the final cycle, the deodorized mercapto acid or a solution of deodorized mercapto acid is collected.

When the procedure is carried out in semi-continuous fashion, the mercapto acid and, where appropriate, the solvent are introduced into a reactor, the reactor is filled with carbon dioxide and it is arranged for the pressure and temperature conditions desired for the extraction to be obtained. A washing flow with gaseous or liquid carbon dioxide is then established for a specified period, which flow may be constant or variable, this flow being dependent on the installation. This flow is generally at between 0.5 and 3 kg/h. It is often preferable to relate this flow to the amount of product treated: it is generally at between 1 and 30 kg/h per kg of mixture subjected to the extraction. Finally, the carbon dioxide is drawn off and the deodorized mercapto acid or a solution of deodorized mercapto acid is collected.

When the procedure is carried out in continuous fashion, the extraction of the mercapto acid is performed with carbon dioxide in liquid or gaseous form employing parallel-flow or countercurrent operation on a separating column. A continuous flow of both the mixture to be extracted and carbon dioxide is established. The ratio of the two flows is fixed so as to obtain the best possible extraction yield.

After separation of the carbon dioxide, the deodorized product collected consists of the mercapto acid and, where appropriate, the greater part of the solvent; it probably contains small amounts of residual $CO_2$. It should be noted that it can contain odorless impurities, these causing no problem.

The deodorized product obtained is preferably packaged carefully, protected from aerial oxygen, in a container known for its chemical compatibility with the mercapto acid, without removing the residual carbon dioxide. Under these conditions, it can be stored for several months without the unpleasant odor due to hydrogen sulphide or to decomposition thiols reappearing at a level that can be detected by one's sense of smell.

The solvent, especially the alcoholic solvent, can, where appropriate, be removed at least partially from the deodorized product, by any known process, before storage.

Irrespective of the extraction process used, the carbon dioxide may be recycled after being relieved of the extracted malodorous compounds according to known methods such as passage through active charcoal.

The subject of the present invention is also the deodorized product obtained by the process defined above.

The deodorized mercapto acids of formula (I) or solutions of deodorized mercapto acid of formula (I) obtained may be used in all industrial applications known for these products. The mercapto acid is generally combined with other ingredients in a composition whose formulation varies according to the application. The efficiency of the deodorization enables them to be used, without imparting an unpleasant odor, in any composition which must not have an unpleasant odor and whose other ingredients do not possess an unpleasant odor. There may be mentioned, as an example, the possibility of combination with thiols such as cysteine or cysteamine which do not have an unpleasant odor.

When the composition used contains ingredients that are liable to cause the benefit of the deodorization to be lost by inducing the formation of malodorous compounds, it can be advantageous to package the mercapto acid or solution of mercapto acid obtained separately, and to prepare the amount of composition needed for the application at the last moment.

The examples given below, as an illustration and without implied limitation, will enable a better understanding of the invention to be gained.

Examples 1 to 3 are examples of deodorization.

EXAMPLE 1

In this example, the extraction was performed in an extraction installation operating in discontinuous fashion shown diagrammatically in attached FIG. 1.

The installation contains a reactor 1 having a capacity of 100 ml, consisting of a pressure-resistant steel casing 1a and a lid 1b. The reactor 1 is equipped with a stirring and heating system shown diagrammatically at 2. The carbon dioxide is stored in liquid form under pressure in a reservoir 3 which is connected to the reactor via a condenser 4 which enables the carbon dioxide to be liquefied. The reactor 1 is equipped with a safety valve 5; it is connected via a valve 6 to a restrictor (not shown in the figure) consisting of a silica tube 30 cm in length and 50 microns in internal diameter which effects slow decompression of the reactor.

50 ml of an aqueous solution of thioglycolic acid containing 92 g/l (1 M) are introduced into the reactor 1. The reactor is then filled with liquid carbon dioxide coming from the reservoir 3 at a temperature of 10° C. and at a pressure of $45 \times 10^5$ pascals. The reactor is isolated and the stirrer is started. The temperature is allowed to rise to room temperature (23° C.). The pressure then reaches $60 \times 10^5$ pascals. Contact is maintained with stirring for 20 minutes. The carbon dioxide is then removed by slow decompression via the restrictor. When the pressure in the reactor reaches $50 \times 10^5$ pascals, the pressure is brought back to $60 \times 10^5$ pascals and the temperature to 23° C. and the mixture is again kept stirring for 20 minutes. A complete decompression of the reactor is then implemented and an aqueous solution of deodorized thioglycolic acid is collected. No odor is detected, and an analysis by gas chromatography shows that there is neither hydrogen sulphide nor methanethiol in the acid.

It is found that, after 1 month of storage protected from air, the thioglycolic acid has not reacquired an odor that can be detected by one's sense of smell.

EXAMPLE 2

50 ml of a solution of thioglycolic acid containing 184 g/l (2 M) are introduced into a 100-ml reactor equipped with a stirrer, and the mixture is heated to 50° C. 100 g of "dry ice" are then introduced gradually with vigorous stirring in such a way that the initial temperature does not change. When all of the "dry ice" has been introduced, the mixture is allowed to cool at room temperature while covered with $CO_2$.

The thioglycolic acid obtained no longer possesses the unpleasant odor it possessed before treatment.

EXAMPLE 3

Figure 2:
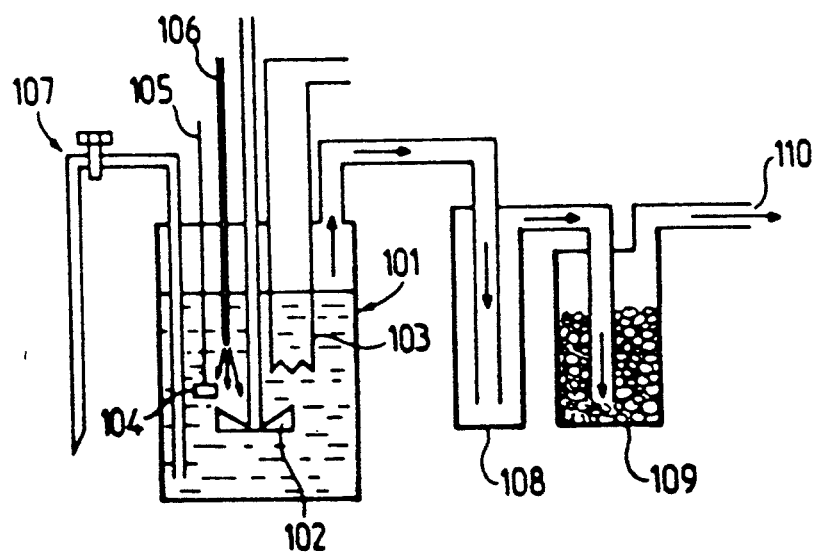
FIG. 2 is also a flow diagram of an extraction process of the present invention.

In this example, the extraction is performed in the installation illustrated in FIG. 2.

This installation comprises a 0.5-liter. reactor 101 equipped with a magnetic or mechanical stirrer 102 and an immersion heater 103. A thermocouple 104, linked to a temperature measuring device 105, enables the temperature to be regulated. A pipe 106 enables carbon dioxide $CO_2$ coming from a source, not shown, to be introduced. On the top of the reactor 101, a pipe is arranged for drawing off the gas contained in the reactor, which enables the gas to pass into a static trap 108. The trap 108 is itself linked at the top to a trap containing active charcoal 109 for trapping the malodorous compounds. The gaseous effluents are drawn off at the top of the trap 109 via a pipe 110. The liquid contained in the reactor 101 is drawn off from the reactor 101 via a tube 107 which dips into the said reactor and which is equipped with tap.

250 ml of an aqueous solution of thioglycolic acid containing 368 g/l (4 M) are introduced into the reactor 101 and, after stirring has been started, the temperature is brought to 40° C. Carbon dioxide is then injected into the solution at a pressure of $250 \times 10^5$ pascals with a flow rate of 3 ml/minute. The gaseous effluent now almost free from malodorous compounds is drawn off at 110. After 3 hours, the reactor is cooled to 20° C. and the aqueous solution of deodorized acid is drawn off via the pipe 107.

The thioglycolic acid obtained no longer possesses the unpleasant odor which it possessed before treatment.

Examples 4 to 11 are examples of use of an aqueous solution of a deodorized mercapto acid of the formula I.

EXAMPLE 4

The following are prepared:
A—A reducing Composition
This preparation is made from two solutions stored in different bottles.

| Solution (a) | | |
|---|---|---|
| Aqueous solution of deodorized thioglycolic acid containing 36% of active substance | | 25 g |
| Solution (b): | | |
| Laurylamine oxide marketed by the company "AKZO" under the name "AROMOX DMMCD/W" | | 2 g |
| Ethylene diaminetetraacetic acid | | 0.15 g |
| Monoethanolamine | qs | ph 9.0 |
| Demineralized water | qs | 75 g |

After the solution (a) is mixed with the solution (b), a reducing composition having a pH of 9.0 is obtained.

This reducing composition is applied to wet hair previously wound on curlers, the hair is then covered with a plastic bonnet and the composition is left to act for 15 minutes at room temperature. The hair is then rinsed copiously with water and the oxidizing composition defined in B is then applied.

B—Oxidizing Composition Having the Following formulation:

| | | |
|---|---|---|
| Hydrogen peroxide | | 2 g |
| Sodium stannate | | 0.015 g |
| Ammonium lauryl sulphate | | 1.4 g |
| Protein hydrolysate | | 0.6 g |
| Citric acid | | 0.5 g |
| Perfume | qs | |
| Demineralized water | qs | 100 g |

The oxidizing composition is left to act for 5 minutes, the hair is then unwound and the composition is left to act for a further 3 minutes. Lastly, the hair is rinsed copiously with water.

After drying under a salon dryer, it is noted that the hair has beautiful locks with a good degree of curling.

The operator's sense of smell failed to detect the development of any nauseating odor during the operation.

EXAMPLE 5

Using the same procedure as that described in Example 4, a permanent-reshaping of hair was carried out using the following reducing and oxidizing compositions:

A—Reducing Composition

| Solution (a) | | |
|---|---|---|
| Aqueous solution of deodorized thioglycolic acid containing 18% of active substance | | 50 g |
| Solution (b): | | |
| Laurylamine oxide marketed by the company "AKZO" under the name "AROMOX DMMCD/W" | | 0.9 g |
| Diethylenetriaminepentaacetic acid pentasodium salt | | 0.15 g |
| Perfume | qs | |
| Ammonia solution (20% in water) | qs | pH 7.8 |
| Demineralized water | qs | 50 g |

On mixing, a composition having a pH of 7.8 is obtained.

B—Oxidizing Composition

The same oxidizing composition as that described in Example 4 is used.

The operator's sense of smell failed to detect the development of any nauseating odor during the operation.

EXAMPLE 6

Using the same procedure as that described in Example 4, a permanent-reshaping of hair was carried out using the following reducing and oxidizing compositions:

A—Reducing Composition

| Solution (a) | | |
|---|---|---|
| Aqueous solution of deodorized thiolactic acid containing 22% of active substance | | 50 g |
| Solution (b) | | |
| Laurylamine oxide marketed by the company "AKZO" under the name "AROMOX DMMCD/W" | | 0.9 g |
| Perfume | qs | |
| Ammonia solution (20% in water) | qs | pH 8.2 |
| Demineralized water | qs | 50 g |

On mixing, a composition having a pH of 8.2 is obtained.

B—Oxidizing Composition

The same oxidizing composition as that described in Example 4 is used.

The operator's sense of smell failed to detect the development of any nauseating odor during the operation.

EXAMPLE 7

Using the same procedure as that described in Example 4, a permanent-reshaping of hair was carried out using the following reducing and oxidizing compositions:

A—Reducing Composition

| Solution (a) | | |
|---|---|---|
| Aqueous solution of deodorized thioglycolic acid containing 18% of active substance | | 50 g |
| Solution (b): | | |
| Cysteine | | 4.5 g |
| Stearic ester polyoxyethylenated with 8 mol of ethylene oxide, marketed by the company "ICI" under the name "MYRJ 45" | | 0.85 g |
| Preservative | | 0.35 g |
| Perfume | qs | |
| Ammonia solution | qs | pH 8.8 |
| Demineralized water | qs | 50 g |

On mixing, a composition having a pH of 8.8 is obtained.

B—Oxidizing Composition

| Hydrogen peroxide (20 volumes) | | 40 g |
|---|---|---|
| Citric acid | qs | pH 3.2 |
| Demineralized water | qs | 100 g |

The operator's sense of smell failed to detect the development of any nauseating odor during the operation.

EXAMPLE 8

Using the same procedure as that described in Example 4, a permanent-reshaping of hair was carried out using the following reducing and oxidizing compositions:

A—Reducing Composition

| Solution (a) | | |
|---|---|---|
| Aqueous solution of deodorized thioglycolic acid containing 18% of active substance | | 40 g |
| Solution (b): | | |
| Cysteamine hydrochloride | | 6.0 g |
| Laurylamine oxide marketed by the company company "AKZO" under the name "AROMOX DMMCD/W" | | 2 g |
| Preservative | | 0.15 g |
| Perfume | qs | |
| Monoethanolamine | qs | pH 7.8 |
| Demineralized water | qs | 60 g |

On mixing, a composition having a pH of 7.8 is obtained.

B—Oxidizing Composition

| Sodium bromide | | 8 g |
|---|---|---|
| Triethanolamine | qs | pH 8 |
| Monosodium phosphate, hydrated (12H$_2$O) | | 0.3 g |
| Trisodium phosphate, hydrated | | 0.5 g |
| Cocamidopropylbetaine marketed by the company "GOLDSCHMIDT" under the name "TEGOBETAINE HS" | | 1 g |
| Perfume | qs | |
| Demineralized water | qs | 100 g |

The operator's sense of smell failed to detect the development of any nauseating odor during the operation.

EXAMPLE 9

The following were used:

A—A Reducing Composition Stored in a Single Bottle and Having the Following Composition

| Aqueous solution of deodorized thioglycolic acid containing 36% of active substance | | 25 g |
|---|---|---|
| Laurylamine oxide marketed by the company "AKZO" under the name "AROMOX DMMCD/W" | | 2 g |
| Ethylenediaminetetraacetic acid | | 0.15 g |
| Monoethanolamine | qs | pH 9 |

| | | |
|---|---|---|
| Demineralized water | qs | 100 g |

This reducing composition is applied to wet hair previously wound on curlers, the hair is then covered with a plastic bonnet and the composition is thereafter left to act for 15 minutes at room temperature. The hair is then rinsed copiously with water and the following oxidizing composition is applied:

B—Oxidizing Composition

| | | |
|---|---|---|
| Hydrogen peroxide | | 2 g |
| Sodium stannate | | 0.015 g |
| Ammonium lauryl sulphate | | 1.4 g |
| Protein hydrolysate | | 0.6 g |
| Citric acid | | 0.5 g |
| Perfume | qs | |
| Demineralized water | qs | 100 g |

The operator's sense of smell failed to detect the development of any nauseating odor during the operation.

EXAMPLE 10

The following are prepared:
A—A Reducing Composition for Straightening, From Two Solutions Stored in Different Bottles

| | | |
|---|---|---|
| Solution (a) | | |
| Aqueous solution of deodorized thioglycolic acid containing 18% of active substance | | 50 g |
| Solution (b): | | |
| Polyacrylic acid marketed by the company "GOODRICH" under the name "CARBOPOL 934" | | 8 g |
| Ammonia solution (20% in water) | qs | ph 8.2 |
| Perfume | qs | |
| Demineralized water | qs | 50 g |

After the solution (a) is mixed with the solution (b), a reducing composition for straightening, having a pH of 8.2, is obtained.

This composition is applied to wet, initially curly hair, and the hair is stroked using a comb so as to make it straight. After an exposure time of 10 minutes, the hair is rinsed copiously with water and the following oxidizing composition is applied:

B—Oxidizing Composition

| | | |
|---|---|---|
| Hydrogen peroxide | | 2 g |
| Sodium stannate | | 0.015 g |
| Ammonium lauryl sulphate | | 1.4 g |
| Protein hydrolysate | | 0.6 g |
| Citric acid | | 0.5 g |
| Perfume | qs | |
| Demineralized water | qs | 100 g |

The oxidizing composition is left to act for 5 minutes and the hair is then rinsed copiously with water.

The operator's sense of smell failed to detect the development of any nauseating odor during the operation.

EXAMPLE 11

A depilatory composition is prepared from two solutions stored in different bottles:

| | | |
|---|---|---|
| Solution (a) | | |
| Aqueous solution of deodorized thioglycolic acid containing 18% of active substance | | 20 g |
| Solution (b): | | |
| Urea | | 5 g |
| Calcium carbonate | | 1 g |
| Cetyl/stearyl alcohol and oxyethylenated cetyl/stearyl alcohol (80:20 mixture) | | 10 g |
| Perfume | qs | |
| Demineralized water | qs | 80 g |

The solution (a) is mixed with the solution (b), and the pH is adjusted to 11.2 by adding calcium hydroxide.

This composition is applied to the skin and left to act for 10 minutes, and the skin is then rinsed copiously with water.

The operator's sense of smell failed to detect the development of any nauseating odor during the operation.

We claim:

1. A process for deodorizing a mercapto acid by extraction of a greater part of malodorous decomposition products contained therein, said process comprising treating said mercapto acid with carbon dioxide at a temperature and pressure so as to maintain said carbon dioxide essentially outside a supercritical region bounded by a temperature of 31° C. and a pressure of $73.8 \times 10^5$ Pascals, said mercapto acid having the formula:

$$HS-A-COOH \qquad (I)$$

wherein
A represents
(i) $-(CH_2)_n-$ wherein n is an integer ranging from 1 to 4,
(ii)

wherein R represents linear or branched $C_1-C_3$ alkyl, or
(iii)

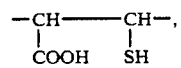

said mercapto acid optionally being in the form of a solution in a polar solvent and said carbon dioxide being in gaseous, liquid or solid form.

2. The process of claim 1 wherein said mercapto acid is thioglycolic acid or thiolactic acid.

3. The process of claim 1 wherein said mercapto acid is directly contacted with said carbon dioxide.

4. The process of claim 1 wherein said polar solvent is selected from the group consisting of water, a linear or branched $C_1-C_5$ monohydric alcohol, a $C_2-C_6$ diol and a $C_3-C_6$ polyol.

5. The process of claim 1 wherein said polar solvent is present in an amount ranging from 1 to 99 percent by weight based on the weight of said mercapto acid.

6. The process of claim 1 wherein said solution of mercapto acid has a mercapto acid concentration ranging from 0.1 mol/liter to 14 mols/liter.

7. The process of claim 1 wherein said extraction is performed in the presence of an inert gaseous compound.

8. The process of claim 1 comprising
   (a) introducing said mercapto acid or a solution thereof, said carbon dioxide and optionally an inert gaseous compound into a reactor,
   (b) establishing in said reactor said temperature and pressure conditions defined in claim 1,
   (c) permitting said mercapto acid, said carbon dioxide and optionally said inert gaseous compound to remain in contact for a period ranging from 5 to 30 minutes,
   (d) drawing off said carbon dioxide,
   (e) optionally repeating steps (a) to (d),
   (f) reintroducing said carbon dioxide into said reactor,
   (g) reestablishing in said reactor said temperature and pressure conditions defined in claim 1,
   (h) permitting said mercapto acid, said carbon dioxide and optionally said inert gaseous compound to remain in contact,
   (i) evacuating $CO_2$ and
   (j) collecting deodorized mercapto acid or a solution thereof 9. The process of claim 1 comprising
   (a) introducing said mercapto acid or a solution thereof into a reactor filled with carbon dioxide,
   (b) establishing in said reactor said temperature and pressure conditions defined in claim 1,
   (c) establishing in said reactor a washing flow of gaseous or liquid carbon dioxide,
   (d) evacuating $CO_2$ and
   (e) collecting deodorized mercapto acid or a solution thereof.

10. The process of claim 9 wherein said flow of carbon dioxide ranges from 0.5 to 3 kg/hr.

11. The process of claim 10 wherein said flow of carbon dioxide ranges from 1 to 30 kg/hr/kg of mixture subjected to said extraction.

12. The process of claim 1 wherein said extraction is carried out in a continuous manner on a separating column with carbon dioxide in liquid or gaseous form.

13. The process of claim 1 which includes recycling carbon dioxide subsequent to removal of said malodorous decomposition products.

* * * * *